United States Patent
Govreen-Segal et al.

(10) Patent No.: US 9,775,703 B2
(45) Date of Patent: *Oct. 3, 2017

(54) LIGHTWEIGHT BREAST IMPLANT MATERIAL

(71) Applicant: G & G BIOTECHNOLOGY LTD., Haifa (IL)

(72) Inventors: Dael Govreen-Segal, Hod Hasharon (IL); Haim Dvir, Nesher (IL)

(73) Assignee: G & G Biotechnology Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/788,350

(22) Filed: Jun. 30, 2015

(65) Prior Publication Data

US 2016/0175486 A1 Jun. 23, 2016

Related U.S. Application Data

(63) Continuation of application No. 13/520,356, filed as application No. PCT/IB2011/050217 on Jan. 18, 2011, now Pat. No. 9,339,371.

(60) Provisional application No. 61/295,788, filed on Jan. 18, 2010.

(51) Int. Cl.
| | |
|---|---|
| *A61F 2/12* | (2006.01) |
| *A61L 27/48* | (2006.01) |
| *A61L 27/52* | (2006.01) |
| *A61F 2/02* | (2006.01) |
| *B05D 3/12* | (2006.01) |
| *A61L 27/44* | (2006.01) |

(52) U.S. Cl.
CPC .............. *A61F 2/12* (2013.01); *A61L 27/446* (2013.01); *A61L 27/48* (2013.01); *A61L 27/52* (2013.01); *A61F 2240/001* (2013.01); *A61F 2250/0015* (2013.01); *A61L 2430/04* (2013.01)

(58) Field of Classification Search
None
See application file for complete search history.

(56) References Cited

U.S. PATENT DOCUMENTS

| | | | | |
|---|---|---|---|---|
| 4,072,635 | A * | 2/1978 | Jeram | 523/218 |
| 4,380,569 | A * | 4/1983 | Shaw | 428/297.4 |
| 4,459,145 | A * | 7/1984 | Elsholz | 65/21.3 |
| 4,650,889 | A | 3/1987 | Plueddemann | |
| 4,861,804 | A * | 8/1989 | Nakanishi | 521/54 |
| 5,055,497 | A | 10/1991 | Okada et al. | |
| 5,258,578 | A * | 11/1993 | Smith et al. | 174/93 |
| 5,902,335 | A * | 5/1999 | Snyder, Jr. | 623/7 |
| 6,194,476 | B1 * | 2/2001 | De Ridder et al. | 521/54 |
| 6,271,278 | B1 * | 8/2001 | Park et al. | 521/150 |

(Continued)

FOREIGN PATENT DOCUMENTS

| | | | |
|---|---|---|---|
| JP | 2002296940 | * | 9/2002 |
| WO | 2006114786 | | 11/2006 |

OTHER PUBLICATIONS

Combined Search Report and Written Opinion for parent PCT Application No. PCT/182011/050217, dated Jul. 5, 2011.

(Continued)

*Primary Examiner* — Peter A Salamon
(74) *Attorney, Agent, or Firm* — Graeser Associates International Inc; Dvorah Graeser (57) ABSTRACT

A prosthetic implant material for use in a prosthetic implant, comprising a gel and optionally a gas.

10 Claims, 6 Drawing Sheets

(56) References Cited

U.S. PATENT DOCUMENTS

| | | | |
|---|---|---|---|
| 6,387,981 B1* | 5/2002 | Zhang et al. | 523/117 |
| 6,486,237 B1* | 11/2002 | Howe et al. | 524/71 |
| 6,733,893 B2* | 5/2004 | Suzuki et al. | 428/447 |
| 6,972,313 B2* | 12/2005 | Howe et al. | 528/15 |
| 7,988,731 B2* | 8/2011 | Govrin-Yehudian et al. | 623/8 |
| 2002/0193878 A1* | 12/2002 | Bowman et al. | 623/7 |
| 2003/0047718 A1* | 3/2003 | Narayan et al. | 252/500 |
| 2003/0144411 A1* | 7/2003 | Howe et al. | 524/588 |
| 2004/0153151 A1* | 8/2004 | Gonzales de Vicente | |
| 2005/0252414 A1 | 11/2005 | Craig et al. | |
| 2008/0203263 A1* | 8/2008 | Carnevali | 248/346.2 |
| 2009/0299473 A1* | 12/2009 | Govrin-Yehudian et al. | 623/8 |
| 2011/0060411 A1* | 3/2011 | Govrin-Yehudian et al. | 623/8 |
| 2012/0277860 A1* | 11/2012 | Dvir et al. | 623/11.11 |

OTHER PUBLICATIONS

Guarding against potential inhibitors /poisons of platinum catalyzed addition cure release coatings published by Dow-Corning as part of their "Facts on File Series", published in 2003.

Ishida, Hatsuo. "Controlled interphases in glass fiber and particulate reinforced polymers: Structure of silane coupling agents in solutions and on substrates." The interfacial interactions in polymeric composites. Springer Netherlands, 1993. 169-199.

JP2002296940—English-translation.

\* cited by examiner

LIGHTWEIGHT BREAST IMPLANT MATERIAL

FIELD OF THE INVENTION

The present invention relates generally to implantable prosthetic devices and specifically to implantable prosthetic devices of reduced weight, featuring material having relatively low density.

BACKGROUND OF THE INVENTION

In the last century reconstructive and cosmetic surgery has become a common practice. Specifically cosmetic breast surgery has been developed to allow reconstruction of a woman's breast that was affected by procedures such as mastectomy. Cosmetic breast surgery has also become available to amend the appearance of a woman's breast, for example by adding an implant to increase the size of the breast, to correct asymmetries, change shape and fix deformities.

For reconstructive and cosmetic surgery, the implant is required to be able to provide a specific three-dimensional shape and maintain the shape for many years, preferably for the lifetime of the woman (or man, depending upon the type of surgery) in which the implant is installed to prevent the need for additional invasive surgery. The implant is also required to have a specific feel, preferably imitating the feel of human tissue, such as the feel of a real breast. The implant also needs to be bio-durable such that it is not ruined by interaction with the human body; and it needs to be bio-compatible so that the patient's health is not detrimentally affected by the implant even under extreme circumstances: for example the implant is required to be non toxic in case of leakage from the implant.

The standard implants used today for breast implant surgery for example comprise an outer shell typically formed from vulcanized silicone rubber (elastomer) which can be single or multi layered, smooth or textured, barrier-coated, or covered with polyurethane foam; and an inner content typically formed from silicone gel or inflated during surgery with saline. An average implant may weigh between 50 to 1000 grams, or even more. The specific weight of the commonly used filling materials is generally between 0.95 to 1.15 grams per cubic centimeter volume, similar to the specific weight of the natural breast tissue.

Nevertheless, natural breast tissue is a live tissue undergoing a common natural lifecycle just as any other tissue within the body, while a breast implant is "dead weight" added to the breast tissue. Both natural breast tissue and breast implants are subjected to forces of gravity. The most common response of both natural breast tissue and breast implants to gravity is sagging over time. The rate of sagging is enhanced in implants as implants are a "dead weight".

Over time breast implants are known to cause many problems, mostly related to the weight of the implant, for example: ptosis (i.e. sagging and deformity), breast tissue atrophy, prominence of the implant through breast tissue, back pain, and striae of the skin. Thus, the weight of the implant is an important factor in post-surgical comfort and appearance.

Traditionally, the silicone gels used as filling materials had silicone oils featuring small liquid molecules such as linear or cyclic silicones, silicone oligomers and low molecular weight silicone polymer chains in them that leached out through the shell over time. Current implants involve the use of a shell with barrier layers to achieve very low permeability of those liquid moieties. In addition, the silicone gel used in breast implants is considered a "cohesive" gel. The cohesiveness ensures that the filling material does not easily flow and spread out into the body, in case of rupture of the shell; it also significantly reduces silicone oil diffusion through the shell.

An additional characteristic to be considered in selection of the filling material is the resilience, elasticity and pliability of the implant, which provides it with a specific feeling when being sensed. Generally it is desirable to provide an implant which provides a specific shape and mimics the feel of real human tissue at the position of the implant. It is important that the implant maintain its form and feel for extended periods, to prevent the need for additional surgery.

US Patent Application Publication No. 2004/0153151 to Gonzales dated Aug. 5, 2004 describes a breast prosthesis from silicone that is formed as a trabecular body or microcell body in order to obtain a prosthesis of lower density.

U.S. Pat. No. 4,380,569 to Shaw dated Apr. 19, 1983 describes a reduced weight breast prosthesis which is worn external to the human body or implanted into the human body. The breast prosthesis is comprised from a mixture of a silicone gel with glass micro-spheres.

U.S. Pat. No. 5,902,335 to Snyder, Jr. dated May 11, 1999 describes a reduced weight breast prosthesis which is worn external to the human body. Snyder states that the use of glass micro-spheres as described by Shaw results in a stiff product that does not mimic the human breast as well as silicone gel alone. Snyder describes a breast prosthesis having two sections. A first outer section filled with silicone gel that mimics the human breast and a second inner section of reduced weight to reduce the weight of the prosthesis.

U.S. Pat. No. 5,658,330, to Carlisle et al. dated Aug. 19, 1997 describes a molded silicone foam implant and method for making it.

SUMMARY OF THE INVENTION

The background art does not teach or suggest a prosthetic implant material which has both sufficiently low density to provide a reduced weight implant and which also has realistic "look and feel" when implanted.

The present invention overcomes these drawbacks of the background art by providing an implant material, which may be regarded as a composite material rather than just a mixture, and that has low density and realistic look and feel upon implantation. The implant material is suitable for use in an encapsulated implant according to at least some embodiments of the present invention, in which the implant features a shell and the implant material, such that the implant material is contained within the shell.

According to preferred embodiments of the present invention, the encapsulated implant is adapted for use as a breast implant.

According to at least some embodiments of the present invention, the implant material comprises a gel, such as for example silicone gel, and a lower density material. Silicone gel density is ~1 gr/cm$^3$ in the order of densities of other liquids, such as water and organic solvents. The lower density material therefore has a density lower than ~1 gr/cm$^3$. Optionally and preferably, the lower density material comprises a gas.

In an exemplary embodiment of the invention, the reduced weight prosthesis may be provided in various sizes, for example extending from 50 cc to 1500 cc or larger or smaller. Optionally, a reduced weight prosthesis may be implanted in other areas of the body other than the breast, for example to replace or augment testicles, pectorals, a chin, cheeks, a calf, buttocks or other parts of the human or an animal body, while exhibiting tactile properties similar to natural tissue.

According to at least some embodiments of the present invention, there is provided a composite material suitable for implantation to the human body, comprising a polymeric gel and a plurality of surface treated additives, wherein the surface-treated additives comprise a surface featuring a reactive cross-linking group for cross-linking to the gel, such that the surface treated additives are cross-linked to the gel. Optionally, the polymeric gel comprises a reactive cross-linking group for cross-linking to the additives and to the gel. Optionally, the polymeric gel comprises a polymer having at least two reactive cross-linking groups per monomeric unit of the polymer. Optionally, the additives comprise a plurality of solid beads.

Optionally the additives comprise a plurality of hollow lumens. Optionally, the plurality of lumens comprises a macro-lumen. Optionally, the plurality of lumens comprises a combination of at least one macro lumen and a plurality of micro-lumens. Optionally the plurality of lumens comprises a plurality of macro lumens arranged in layers.

Optionally the additives comprise a plurality of hollow micro-lumens. Optionally the micro-lumens contain a gas. Optionally the micro-lumens contain at least a partial vacuum up to 0.9 atm.

Optionally the micro-lumens withstand pressures of over 300 psi (>20 Atm) without breaking or collapsing.

Optionally the micro-lumens are constructed of ceramic, plastic, glass, PMMA (polymethyl methacrylate), polyacrylonitrile, polybutadiene, natural or synthetic rubber.

Optionally the micro-lumens are not rigid then the material comprises up to 90% v/v micro-lumens.

Optionally the micro-lumens have a diameter from 1 micron to 500 microns.

Optionally the micro-lumens have a plurality of different diameters.

Optionally the surface features a molecule selected from the group consisting of a long chain fatty acid, another long organic chain, a polymer brush; polystyrenes, organofunctional silanes, zirconates, and titanates. Optionally the polymeric gel comprises silicone gel. Optionally the silicone gel comprises PDMS or a derivative thereof.

Optionally the additives are homogenously dispersed in the gel.

Optionally the composite material is adapted to mask the additives from a tissue by the polymeric gel.

According to at least some embodiments of the present invention, there is provided a prosthetic implant, comprising a shell and the composite material as described herein. Optionally the composite material comprises up to 60% volume/volume micro-lumens with regard to the polymeric gel. Optionally the implant has a volume from 50 cc to 1500 cc.

Optionally the shell comprises a plurality of layers.
Optionally the shell comprises a silicone elastomer.
Optionally the shell further comprises polyurethane foam overlaid on an outer surface of shell.

Optionally the implant comprises a plurality of shells, including at least one inner shell and at least one outer shell, wherein the at least one inner shell is at least partially surrounded by the outer shell, wherein the outer shell is filled with the composite material having a first percentage of micro-lumens and wherein the inner shell is filled with the composite material having a second percentage of micro-lumens, wherein the first and second percentages are different.

Optionally a ratio between the first and second percentages is in a range of from 1:1 to 1:5.

Optionally the first percentage is 30% volume/volume and wherein the second percentage is 50% volume/volume.

According to at least some embodiments, there is provided a method of manufacturing implant as described herein, comprising mixing the polymeric gel and the additives, filling the polymeric gel and the additives in the shell, and rotating the shell during curing.

Optionally the polymeric gel comprises silicone and wherein the silicone is prepared from a plurality of components, the method further comprising mixing the plurality of components of the silicone before mixing in the additives.

Optionally the method further comprises drying the additives before mixing the additives into the silicone.

According to at least some embodiments, there is provided a method of therapeutic, esthetic and/or cosmetic treatment, comprising implanting the prosthetic implant as described herein in a subject.

Optionally the method comprises implanting the implant to replace or augment a breast, a testicle, a pectoral, a chin, a facial cheek, a calf, or a buttock.

According to at least some embodiments, there is provided a prosthetic implant, comprising a shell, a polymeric gel and a plurality of hollow micro-lumens, wherein the micro-lumens comprise a surface, wherein the surface comprises a treatment for interacting with the polymeric gel to form a covalent or non-covalent bond, wherein the polymeric gel and the micro-lumens are contained within the shell.

Optionally the covalent or non-covalent bond increases adhesion of the micro-lumens to the polymeric gel.

Optionally the treatment comprises bonding of a plurality of molecules to the surface.

Optionally the plurality of molecules is selected from the group consisting of a long chain fatty acid, another long organic chain, a polymer brush; polystyrenes, organofunctional silanes, zirconates, titanates, and a molecule for increasing electrostatic interactions.

Optionally the plurality of molecules comprises n-propyltrimethoxysilane.

Optionally the polymeric gel comprises a silicone gel.

Optionally the silicone gel comprises PDMS or a derivative thereof.

Optionally the plurality of molecules comprises n-propyltrimethoxysilane, and the n-propyltrimethoxysilane and the silicone gel undergo a catalyzed curing reaction to cross-link the n-propyltrimethoxysilane to the silicone gel.

Optionally the treatment comprises roughening the surface.

Optionally the composite material comprises up to 60% volume/volume micro-lumens with regard to the polymeric gel.

Optionally the prosthetic implant has a volume from 50 cc to 1500 cc.

Optionally the shell comprises a plurality of layers.
Optionally the shell comprises a silicone elastomer.
Optionally the shell further comprises polyurethane foam overlaid on an outer surface of shell.

Optionally the implant comprises a plurality of shells, including at least one inner shell and at least one outer shell, wherein the at least one inner shell is at least partially surrounded by the outer shell, wherein the outer shell is filled with the composite material having a first percentage of micro-lumens and wherein the inner shell is filled with the composite material having a second percentage of micro-lumens, wherein the first and second percentages are different.

Optionally a ratio between the first and second percentages is in a range of from 1:1 to 1:5.

Optionally the first percentage is 30% volume/volume and wherein the second percentage is 50% volume/volume.

Optionally the micro-lumens are homogenously dispersed within the gel.

According to at least some embodiments there is provided use of a surface treatment on a surface of a micro-lumen in a polymeric gel to mask the micro-lumen from a biological tissue, wherein the surface treatment comprises a reactive cross-linking group attached to the surface, wherein the reactive cross-linking group forms a covalent cross-linking bond with the polymeric gel.

According to at least some embodiments there is provided use of a surface treatment on a surface of a micro-lumen in a polymeric gel to provide a more radio-lucent (permeable to x-ray) implant, wherein the surface treatment comprises a reactive cross-linking group attached to the surface, wherein the reactive cross-linking group forms a covalent cross-linking bond with the polymeric gel and wherein the use further comprises preparing an implant with the cross-linked polymeric gel/micro-lumen.

It should be noted that the composite material as described herein may optionally be implemented as an external prosthesis and/or other external, wearable elements, including but not limited to soles for shoes, a bullet proof vest or other items of clothing.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention provides an implant material that has low density and realistic look and feel upon implantation, which according to at least some embodiments comprises a composite material featuring a gel, such as silicone gel for example, and an additive, which may optionally contain a gas. The implant material is preferably contained within a shell to form an encapsulated prosthetic implant. At least the shell, but preferably all of the materials of the implant, is biologically compatible and safe for therapeutic and/or cosmetic use internally to the human body. The additive may optionally comprise any three dimensional object, whether solid or hollow, and may for example comprise at least one lumen, which may optionally be a macro-lumen or a micro-lumen, or a combination thereof. As described herein, the micro-lumens may optionally take any suitable form, including but not limited to microspheres, micro-lumens or micron sized particles such as porous particles to form a composite material.

Micro-lumens

According to some embodiments, the gas comprises micron sized micro-lumens, which may optionally for example be implemented as hollow micro-lumens. The micro-lumens may optionally be made of rigid materials, including but not limited to glass, ceramic, etc. However, rigid materials may optionally have lower concentration in the gel due to low packing factor where the micro-lumens are in contact with one another. The packing factor may be increased to some extent by using polydispersity of particle sizes. Therefore according to at least some embodiments of the present invention, the micro-lumens comprise particles of a plurality of different sizes, preferably of at least 20% difference between them. In any case, the micro-lumens may optionally have a diameter which is more preferably from 1 micron to 500 microns.

According to at least some embodiments of the present invention, the micro-lumen comprises one or more soft or flexible materials such as polymers, such PMMA (polymethyl methacrylate), polyacrylonitrile, polybutadiene (or any other natural or synthetic rubber or similar materials) for example, or any other amorphous or semi-crystalline polymer. The materials may optionally be determined according to their relative flexibility. For example, for PMMA, the tensile strength at yield is preferably from 52 to 71 mega-Pascal and the tensile modulus is preferably from 2.2 to 3.1 giga-Pascal. For these more flexible polymers, the packing factor may be increased up to an order of ~0.9 and above, such that the boundaries between two adjacent micro-lumens are in surface contact as for soap bubbles, as opposed to tangent contact in rigid spheres. More preferably, a blend of polymers is used, for example a blend of a polymer such as PMMA and a rubbery material such as polybutadiene for example.

The terms "micro-lumen" and "micro-sphere" are used interchangeably throughout the text.

Macro-lumens

According to at least some other embodiments, the gas is provided in the form of at least one macroscopic lumen which contains the gas. The lumen may optionally comprise a single lumen in different geometries, including one or more of a semi-sphere, a disk or other shape attached to a portion of the shell, for example at the back side of the shell; a lumen floating within the gel.

The at least one macro lumen may optionally comprise a plurality of lumens; however, preferably the total volume of the plurality of macro lumens has the same or similar volume to the single larger macro lumen. The shapes may be small spheres or "spaghetti" like rods floating within the gel. The shaped lumens may optionally comprise a plurality of stacked layers, whether flat or with curvature; in the latter case, the curvature is preferably determined according to the implant shape. Each macro lumen may optionally have an internal or external structural element(s), or a combination thereof, for maintaining the three-dimensional shape of the lumen, including but not limited to a beehive, etc.

Combinations of Lumens

In order to further decrease the implant weight, according to at least some embodiments of the present invention, combinations of a gel with microspheres and macroscopic lumens filled with gas may be incorporated. In such an arrangement, preferably the microsphere-containing gel preferably at least partially surrounds the macroscopic lumen(s), more preferably in a portion of the shell that is located closest to the skin or is otherwise closer to a portion of tissue that may be felt through external touch. For example, the interior of the shell of the prosthesis could optionally be arranged with an outer layer of 50% v/v microspheres, mid layer of 30% v/v microspheres and an inner macro-lumen filled with gas.

Composite Materials

According to at least some embodiments of the present invention, the implant comprises a composite material formed through a combination of, and interaction between, additives such as micro-lumens and gel (or optionally between one or more macro-lumens and gel). The term "additive" may optionally comprise any three-dimensional shape having a treatable surface.

A polymer composite may be viewed as a blend of several additives possessing different and distinct functionalities and a polymer matrix that binds and links them together for the purpose of forming a polymer-based material with improved properties well above the intrinsic properties of the polymer or to grant it new properties, such that the composite material described herein may be clearly contrasted with background art gel/glass microsphere mixtures.

According to the background art, glass microspheres are added to a silicone gel which is a crosslinked polymer network to form a simple mixture, in which the gel is the continuous phase and the microspheres are the dispersed phase. In such a simple mixture, each component maintains its own properties, such that the mixture's density is reduced according to a simple linear combination of the two materials.

By contrast, the composite material according to at least some embodiments of the present invention has composite properties which depend not only upon the additives such as micro-lumens (e.g. glass microspheres) and their fractional volume, but also upon interactions with the gel such as the polymer network and the interfacial parameters (compatibility, wettability and bonding, described collectively herein as "adhesion"). Adhesion is important to achieve improvement in composite properties. Adjusting adhesion also increases physical-chemical suitability of the additive to the polymer network, thereby increasing dispersion of the additive in the network.

Surface modification of the additive is a pathway for increasing the adhesion between the polymer and the additive. The adhesion forces between the surface treated additive and the polymer range from strong chemical bonds or electric attraction to weak van der Waals (VDW) interactions, as well as combinations thereof.

The surface treatment supports chemical reaction and/or physical interaction between the lumen and the gel; optionally the macro-lumen may also be surface treated. The reaction preferably prevents the gel and the lumen(s) from separating into two phases. Chemical surface treatment is more preferred, as it induces covalent interactions, which stabilize the lumen(s) within the gel and prevent slippage or separation into two phases. Also the bonding of micro-lumens to the gel causes the gel to surround the micro-lumens; in the event of rupture or leakage, without wishing to be limited by a single hypothesis, it is expected that the gel will continue to cover the micro-lumens, such that the body would only be exposed to the cohesive gel.

Without wishing to be limited by a closed list, some non-limiting examples of surface treatment are provided below. One type of interaction of silicone polymer (in the silicone gel) and the surface of the micro-lumens may optionally be obtained through the use of surface anchored long molecular weight chains. These chains may favor non-covalent molecular entanglements with the gel polymer surrounding the micro-lumen, particularly when the chain is chemically and sterically similar to the polymer. A non-limiting example of such a surface modification is a micro-lumen surface treated with any long chain fatty acid, such as stearic acid for example (chain length of 18 carbons), or any other long organic chain, hydrophobic or hydrophilic molecules depending on the type of favored interaction, including but not limited to polymer brushes; and/or polystyrenes and other such molecules. The term "polymer brush" refers to an assembly of polymer chains which are tethered (grafted, anchored) by one end to a surface or interface. Tethering of the chains in close proximity to each other forces the chains to be oriented away from the surface to avoid overlapping due to the volume-excluded effect.

Another type of surface treatment is creation of a charged surface that favors electrostatic attraction. The forces of attraction between oppositely charged groups on the surface and on the polymer chain are responsible for this interaction. Such interaction is common in acid-base interactions or ion bonding. This type of surface treatment requires a modification of the surrounding gel polymer, such as for example the addition of polyelectrolyte to silicone gel.

Yet another type of surface treatment involves increasing the "roughness" or physical variability of the surface of the micro-lumens, such that parts of the surface project out into the gel and hence may interact with the gel.

Yet another type of interaction is chemical bonding between the surface and the polymer matrix molecules achieved by the use of coupling agents. Most cases of surface treatment by organofunctional silanes, zirconates, titanates and other coupling agents result in this type of polymer-surface interaction. The type of coupling agent is selected according to the surface chemistry of the additive, in this case, the chemical composition of the surface of the micro-lumens and hence the material that is suitable for use with the micro-lumens.

Organofanctional silanes are mostly used to improve mechanical properties and to maintain them by protecting the surface from moisture and heat that cause property deterioration. During composite processing, storage and usage, water from the surroundings diffuses through the matrix. This moisture affects the wettability of the glass by reducing the surface energy from ~500 mJ/m$^2$ for pure glass to ~10-20 mJ/m$^2$ for wet glass, and promotes corrosion on specific sites on the surface. In order to ensure good wetting of a solid by a liquid, the liquid phase should have a surface energy lower than that of the solid surface. The low value for the wetted glass is well below that of the polymer matrix, which results in reduced wettability, increased adhesive failure and enhanced overall property deterioration. Thus, the use of bare glass micro-lumens is inadequate in implants over the long term; such problems are overcome through the use of functional derivatization of the micro-lumen surface as described herein.

The most common chemical structure of the silane is R—Si—X$_3$ where X is an alkoxy group that may hydrolyze to reactive groups on the surface and R is organofunctional group the can react with the polymer matrix. There are two main techniques for the insertion of the silane:

a. Pretreatment—the direct application of the pure silane or its solution in an organic solvent diluted with water which accelerates the reaction, to the additive. Usually, this technique is accomplished by spraying or immersing the additive with the silane agent (surface finish).

b. Addition of the silane to the polymer followed by the untreated additive. This technique is used less frequently but is still contemplated for at least some embodiments of the present invention.

The result of such surface treatment is the formation of a thick three-dimensional crosslinked silane multi-layer, polysiloxane network. Silane monolayer, obtained for example through the use of vapor phase silylation techniques, may also optionally be used.

For example, silanes are used to form chemical bonds to the surface of glass and so may optionally be used with micro-lumens of glass. The organofunctional group of the silane is selected according to the type of interaction that is favorable between the polymer and the additive. The interaction may be of the order of weak VDW forces, hydrophilic-hydrophobic interactions and up to chemical covalent bonds. There is a large variety of possible R groups and the specific species is selected by its affinity to the polymer matrix. It should be noted that more than one type of silane might be effectively used with a given polymer. Thus, for a specific polymer, the most suitable organofunctional silane coupling agent selected should result in chemical bonding and interdiffusion through the matrix to form a network with the polymer, For example, surface treatment with a silane such as n-propyltrimethoxysilane may increase the affinity of the hydrophobic silicone gel to the glass; a non-limiting example of such a silicone gel is a gel comprised of Polydimethylsiloxane (PDMS) chains. Also it may take part in the chemical reaction occurring during the gel curing stage and thus form better bonding with the silicone gel. The wetting angle of a glass surface coated with n-Propyltrimethoxysilane is in the range of 80 degrees and above compared to a wetting angle of bare glass which is below 20 degrees; as noted previously, increased wetting angle leads to increased glass/gel interactions and better distribution of the micro-lumens.

One non-limiting example of a suitable curing mechanism is a platinum catalyzed addition reaction between the silane and the glass. It consists of a vinyl substituted PDMS that is cross-linked with a hydrogen substituted PDMS as the crosslinker. Hydrogen substitution means that a few silicon atoms in the PDMS chain have a vinyl group instead of a methyl group. The vinyl group is susceptible of bonding to a neighboring chain with a few silicon atoms of the PDMS that have a hydride group instead of a methyl group, creating a cross-link. Each silicon hydride group is added across a vinyl double bond ($CH_2$=CH—), thereby converting the vinyl group to an ethylene (—$CH_2$—$CH_2$—) bridge linking two silicone polymer molecules together.

Since at least some of the silicone polymer molecules are expected to have more than two reactive groups per molecule but without wishing to be limited by a single hypothesis, the reaction is expected result in a cross-linked system without adding any new soluble or leachable components. This curing reaction is known as hydrosilation and it forms a very lightly cross-linked gel that gives the desired softness and compliance or resiliance (i.e. —the desired "look and feel" of actual tissue). The propyl moiety of n-Propyltrimethoxysilane may take the role of the hydrogen substituted PDMS and act as a crosslinker. Thus, the hydrosilation curing reaction also occurs on the surface treated microlumens and results in a cross-linked system without adding any new soluble or leachable components.

Another possibility is 3-Glycidoxypropyltrimethoxysilane which may participate in the chemical reaction occurring during the gel curing phase resulting in better bonding to the silicone gel. The epoxy functional silane is less hydrophobic than propyl functional silane, but is more reactive in the same reaction conditions. Again, the surface treatment may act as a crosslinker.

Through such chemical cross-linking and other interactions, gel polymer is accumulated at the polymer/micro-lumen interface, adsorbed on the surface of the surface treated additive, involves the formation of physical interactions and chemical bonds, denoted as physisorption and chemisorption, respectively. Without wishing to be limited by a single hypothesis, it is reasonable to assume that the most strongly adhered polymer chains remain on the surface and that the adsorption is irreversible and permanent, such that the initially contacting chains are retained and adsorbed onto the surface, covering the entire micro-lumen. Thus, even if the implant were to rupture, no direct contact between the tissue and the additive would occur. The surrounding tissue would only contact the external covering layer of gel on the surface of the additive. The micro-lumen would therefore form an intrinsic part of the gel network, acting as a crosslinking site within the network.

In addition, due to the combination of the physical attraction on the surface and the covalent bonds, without wishing to be limited by a single hypothesis, it is likely that the overall adhesion strength between the treated glass surface and the gel is higher than the cohesion strength within the gel. Thus, failure of the composite material due to external applied force, such as a physical blow, would result in loss of integrity within the gel and not at the gel-additive interface. This is not true for untreated or inadequately treated additives for which failure may occur at the interface, as already mentioned above, as the gel/additive combination is a mixture rather than a composite.

Also, for a composite material, mechanical properties such as elastic modulus may be controlled, for example by being increased above the level expected for an untreated or inadequate treated microspheres and gel mixture, optionally from at least about twice as elastic to about ten times as elastic. There is an increase in certain mechanical properties in such a mixture due to the addition of high modulus microspheres which may mask the detrimental effect of the micro-lumens in reducing gel network continuity. On the contrary, there is an additional increase of certain mechanical properties such as elastic modulus due to the fact that treated micro-lumens integrate within the polymer network. As described in greater detail below, this effect has been experimentally demonstrated (see FIG. 6).

Optionally, the additives can be coated with gel which is then cured rapidly, after which the gel/additive combination may optionally be mixed with other materials, including gel for example.

Gel Material

The above described polymer gel is preferably a silicone gel as is known in the art, such as PDMS and derivatives thereof for example, and/or any other suitable polymer gel; in the case of implanted composite material the gel is biocompatible.

Shell Material

The implant is preferably encapsulated by a shell, constructed of a material as is known in the art, for containing the above described composite material. A non-limiting example of a suitable shell material is a silicone elastomer, optionally with a material such as polyurethane foam overlaid on the shell.

The principles and operation of the present invention may be better understood with reference to the drawings and the accompanying description.

EXAMPLE 1

Physical Structures of Implants

FIGS. 1-5 show various non-limiting exemplary embodiments of implants according to the present invention. Any of the above described embodiments of shell material, gel material and micro-lumens/macro-lumen(s) (or combinations thereof) may optionally be used with the below described structures.

Figure 1:
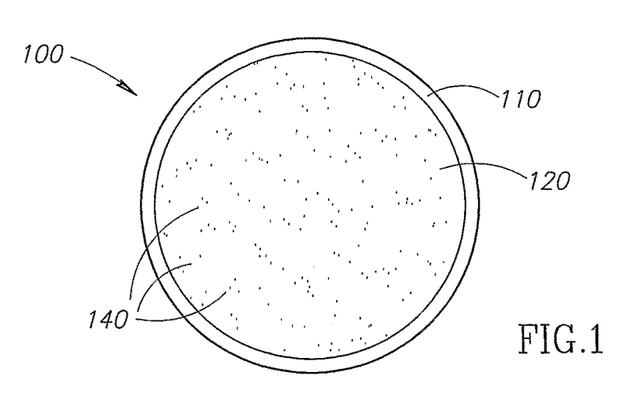
FIG. 1 shows a non-limiting example of an illustrative encapsulated prosthetic implant according to at least some embodiments of the present invention.

FIG. 1 shows a non-limiting example of an illustrative encapsulated prosthetic implant according to at least some embodiments of the present invention. As shown, an implantable prosthesis 100 comprises a low penetratable shell 110 that optionally comprises a biocompatible silicone, polyurethane or other material as is commonly used for implants. Shell 110 may comprise a single layer or multiple layers, wherein some layers may be from one material and others from another. Additionally, shell 110 may be smooth or textured, with various patterns. Shell 110 can have areas of varying elasticity. Shell 110 can have a different thickness in different areas. Optionally, the material of shell 110 may be a combination of several materials. Generally, shell 110 serves as an enclosure for preventing the content of prosthesis 100 from leaking out. Optionally, shell 110 may be provided in various shapes, for example round, oval, anatomical, custom or other.

Shell 110 contains a gel 120 and at least one lumen 140. In this non-limiting example, shell 110 contains a plurality of micro-lumens 140, which may optionally be flexible or "soft", or rigid or "hard". Micro-lumens 140 may optionally for example be implemented as hollow micro-lumens.

Figure 2:
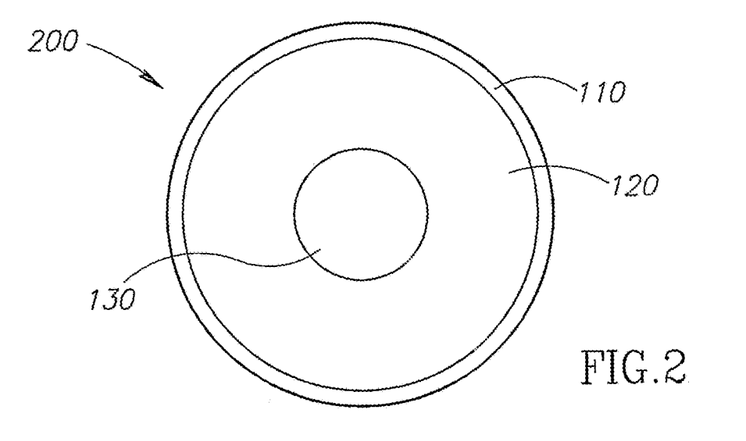
FIG. 2 shows another non-limiting example of an illustrative encapsulated prosthetic implant according to at least some embodiments of the present invention.

FIG. 2 shows another non-limiting example of an illustrative encapsulated prosthetic implant 200 according to at least some embodiments of the present invention. In this example, shell 100 again contains gel 120; however the at least one lumen comprises a macro-lumen 130 as shown.

Figure 3:
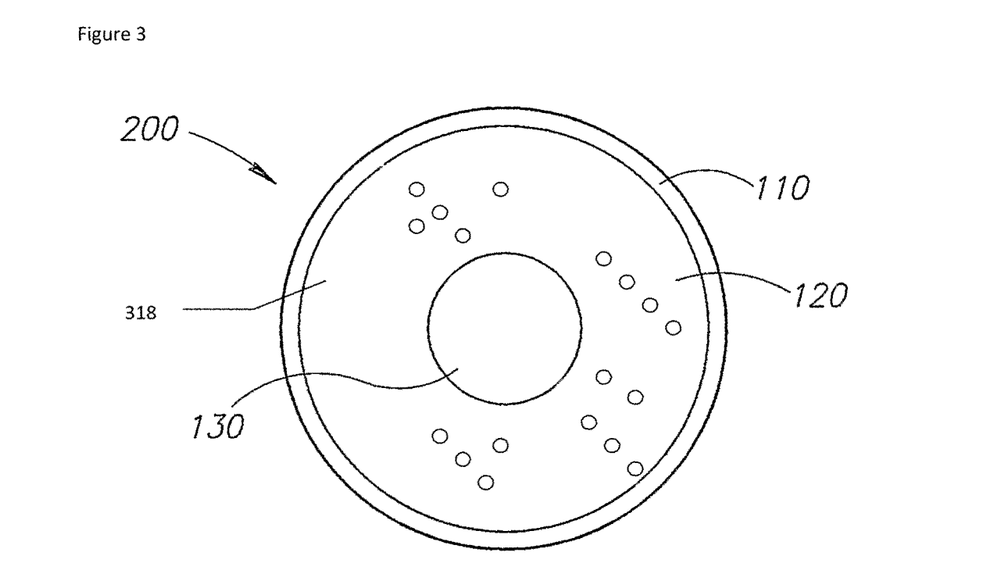
FIG. 3 shows yet another non-limiting example of an illustrative encapsulated prosthetic implant according to at least some embodiments of the present invention.

FIG. 3 shows yet another non-limiting example of an illustrative encapsulated prosthetic implant 300 according to at least some embodiments of the present invention. In this example, shell 110 again contains gel 120; however the at least one lumen comprises a macro-lumen 130 as shown, on top of which is provided a layer 318, comprising gel 120 mixed with a plurality of micro-lumens 314. By "top" it is preferably meant a location closer to the skin.

Various other arrangements of the shell 110/210/310 and/or other components which are taught in US Patent Application No. 20090299473, filed on Apr. 24 2006, hereby incorporated by reference as if fully set forth herein, which is co-owned in common with the present application and which has at least one inventor in common, may also optionally be used, additionally or alternatively.

If the lumen comprises a rigid micro-lumen or plurality thereof, such as rigid microspheres for example, the relative amount of such rigid micro-lumens is preferably less than 60% v/v in the gel. For example, as the concentration of microspheres was increased up to 60% v/v in Silicone gel, the firmness of the gel increased and the elongation property decreased. Above 60% v/v of micro spheres, the mixture behaves like a paste.

To reduce the adverse effect of firmness and lack of flexibility of the resultant gel mixture, different layers of gel with different microsphere concentrations are preferably provided, more preferably with an increased concentration of microspheres in a portion of the shell which is farthest away from the skin or which is otherwise less likely to be "felt", with decreasing concentrations of microspheres away from this location, optionally even up to a layer with no microspheres. A non-limiting example of such a layer arrangement is as follows: 40% volume of the implant filled with 50% v/v microspheres in an inner lumen and the rest of the implant filled with 30% v/v microspheres.

Figure 4:
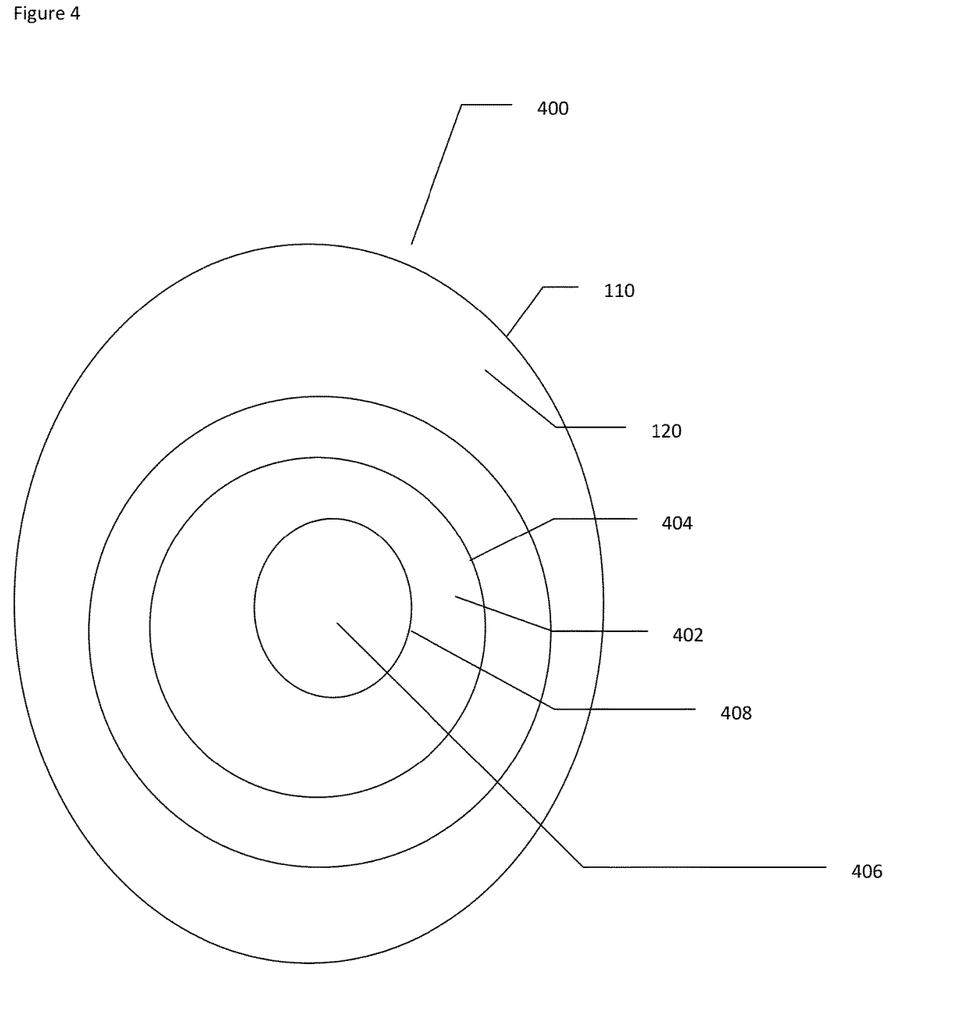
FIG. 4 shows still another non-limiting example of an illustrative encapsulated prosthetic implant according to at least some embodiments of the present invention.

FIG. 4 shows another arrangement of yet another non-limiting example of an illustrative encapsulated prosthetic implant 400 according to at least some embodiments of the present invention. In this example, shell 110 again contains gel 120. Within gel 120, there is a first macro-lumen 402 as shown, which preferably features a plurality of micro-lumens mixed with gel (not shown), surrounded by another shell 404. Within first macro-lumen 402, there is preferably a second macro-lumen 406 which only features air, as the innermost layer, which again is encapsulated by yet another shell 408. Each of shell 110, 404 and 408 may optionally be made of similar or different materials. Also any of the above mentioned embodiments may optionally be combined with this embodiment.

Figure 5A:
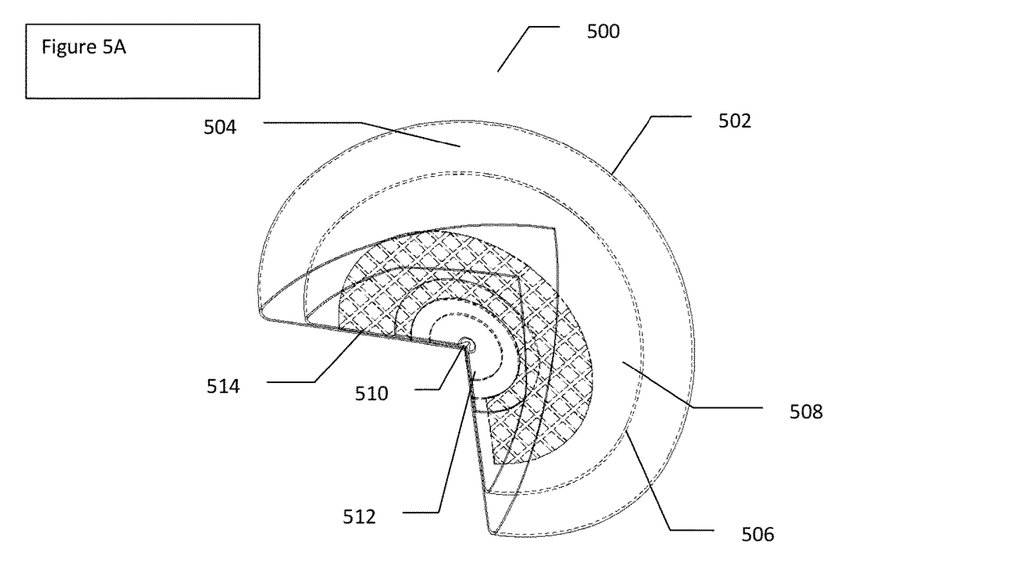
FIGS. 5A and 5B show another arrangement of yet another non-limiting example of an illustrative encapsulated prosthetic implant according to at least some embodiments of the present invention.
Figure 5B:
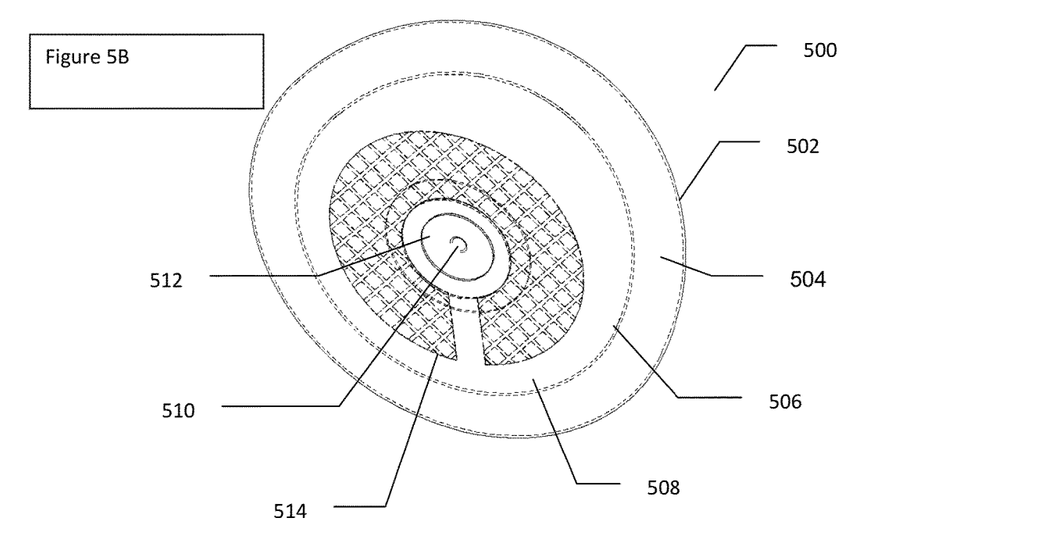

FIGS. 5A and 5B show another arrangement of yet another non-limiting example of an illustrative encapsulated prosthetic implant 500 according to at least some embodiments of the present invention. FIG. 5A shows a partially cut-away view of the implant, while FIG. 5B shows the whole implant with "transparent" boundaries. In this example, an outer shell 502 contains an outer composite material 504, while an inner shell 506 contains an inner composite material 508. Each of outer shell 502 and inner shell 506 may optionally be constructed for a silicone elastomeric material as described herein, optionally with a plurality of layers and also optionally with a barrier layer. Outer shell 502 may optionally feature any of a smooth, non-textured surface; a textured surface; or a micro polyurethane foam coated surface. Surface texturing has been shown to reduce the incidence and severity of capsular contraction. Inner shell 506 is preferably smooth but may also optionally be textured.

Outer composite material 504 preferably features a smaller volume/volume percentage of micro-lumens within a gel, such as glass microspheres for example, than inner composite material 508. By "smaller" it is meant that the volume/volume percentage ratio of micro-lumens in outer composite material 504 to that in inner composite material 508 optionally ranges from 1:5 to 1:1. As a non-limiting example, outer composite material 504 may optionally comprise 30% volume/volume microspheres while inner composite material 504 may optionally comprise 50% volume/volume microspheres.

Each of outer shell 502 and inner shell 506 is closed with a patch made of the same silicone elastomers as the respective shell 502 and 506, and glued using an adhesion component, with small silicone cap 510 on the inner side of the posterior lumen patch 512, used for gel filling. Inner shell 506 is situated concentrically within outer shell 502 and glued to it at a base 514.

EXAMPLE 2

Surface Treatment of Micro-lumens

This Example relates to a non-limiting, illustrative method for treating the surface of micro-lumens. In this Example, the micro-lumens are assumed to have a glass surface and to be treated with a silane, which may optionally be any suitable silane as described. In terms of the actual materials used for preparing the glass microspheres of Example 3, hollow borosilicate glass microspheres were coated with n-Propyltrimethoxysilane. The mean size of the microspheres was approximately 60 µm (20 µm to 140 µm) in diameter.

Specifically, the glass in the microspheres featured 1% Sodium; 2% Boron; 96.5% Silica; and 0.5% Trace (mostly calcium oxide, and other common earth oxides).

The gas mixture inside the microspheres was composed of approximately: 55% nitrogen; 37% carbon dioxide; 7.6% oxygen; and 0.4% Argon. The pressure of the gas mixture within the microspheres is 0.5 atm. Of course other gas mixtures could be used instead.

The microspheres used typically withstand pressures of over 300 psi (>20 Atm) without breaking or collapsing as a non-limiting but preferred example.

The microspheres were subjected to a similar procedure to that described below for treating and derivatizing the glass surface.

Procedure for Silane Surface Treatment
1. Glass Cleaning Solution Preparation:
   35 ml of Potassium dichromate ($K_2Cr_2O_7$) saturated solution is added slowly to 1 L of concentrated sulfuric acid ($H_2SO_4$) solution in a temperature controlled environment due to a highly exothermic response. The entire sulfochromic solution is agitated for approximately 15 min where a brownish solution appears. It is recommend to use fresh solution for each cleaning procedure.
   Piranha solution is used to clean organic residues off glass and make it more hydrophilic by hydroxylating the surface, thus increasing the number of silanol groups on the surface. The traditional piranha solution is a 3:1 mixture of sulfuric acid ($H_2SO_4$) and 30% hydrogen peroxide ($H_2O_2$). Other ratios have been used ranging from 1:1 to 7:1. The solution may be mixed before application or directly applied to the glass, applying the sulfuric acid first, followed by hydrogen peroxide. $H_2O_2$ is added very slowly to the $H_2SO_4$. The solution should begin to bubble vigorously and heat due to highly exothermic response. Due to the self-decomposition of hydrogen peroxide, piranha solution should be used freshly prepared.
2. Glass Cleaning:
   The glass microspheres are placed and left in the cleaning sulfochromic solution for a 1.5 hour period of time. Later, the glass microspheres are rinsed for 5 min in distilled water twice and subsequently twice in methanol in order to remove excess cleaning solution. The glass is air dried.
   The glass is placed and left in the cleaning piranha solution for a 10 min period of time. Later, the glass microspheres are rinsed for 5 min in distilled water twice in order to remove excess cleaning solution. The glass is air dried.
3. Silane Treatment Solution Preparation (2% Silane in Total Volume):
   93.25% vol. Methanol is mixed with 3.93% vol. of distilled water. 0.81% vol. Acetic acid is added to buffer the solution to a pH of 4.5-5.5. 2% vol. of the functional silane is added to the solution.
4. Silane Treatment:
   The solution is agitated for 10 min and during that time, silanol groups are formed in the solution. The clean glass is introduced to the solution for approximately 5 min. Then, the glass is rinsed twice in pure methanol and inserted to a 105° C. oven for 10 min in order to cure and finalize the procedure to form the silane layer.

EXAMPLE 3

Preparation of an Exemplary Implant

This illustrative Example relates to a method of preparation of an implant according to at least some embodiments of the present invention. For the purposes of description only and without wishing to be limited, the process relates to preparation of an implant according to FIG. 5 above, featuring an outer compartment with 30% microspheres/gel volume/volume and an inner compartment with 50% microspheres/gel volume/volume. The microspheres used are those described in Example 2 above, which underwent surface treatment as described above. In the procedure described below, a 390 cc in volume implant with a posterior lumen of 175 cc in volume and an anterior lumen of 215 cc in volume is addressed as an example.

The implant features a plurality of standard silicone shells which are currently used in the breast implant industry. In this Example, the shells were MED-6640 (NuSil Technology), with a barrier layer—MED-6600 (NuSil Technology) which features phenyl-derivatized PDMS.

Adhesion between the shell and patch was provided with MED-4750 (NuSil Technology); the patch seals the opening to the shell and in this example features a septum for permitting filling of the shell.

The filling material was a mixture of an unrestricted grade of Silicone gel used in the breast implant industry (MED3-6300 (NuSil Technology)) and specially customized hollow glass microspheres, prepared as described in Example 2 from hollow borosilicate glass microspheres coated with n-Propyltrimethoxysilane.

For preparation of the posterior/anterior (inner/outer) lumens, the below amounts of microspheres and Silicon Part A and Part B were used, as shown in tables 1 and 2.

TABLE 1

Dispersion composition, posterior, 175 cc

| Component | Content (% v) | Content (gr) | Accuracy (±gr) |
|---|---|---|---|
| Silicone, Part A | 37.5 | 63.66 | 0.01 |
| Silicone, Part B | 12.5 | 21.22 | 0.01 |
| Microspheres | 50 | 14.00 | 0.01 |

TABLE 2

Dispersion composition, anterior, 215 cc

| Component | Content (% v) | Content (gr) | Accuracy (±gr) |
|---|---|---|---|
| Silicone, Part A | 52.5 | 78.21 | 0.01 |
| Silicone, Part B | 17.5 | 26.07 | 0.01 |
| Microspheres | 30 | 10.32 | 0.01 |

The silicone gel is composed of a two part kit in a two component system which cross-link only upon mixture (for example, one part will feature the polymer with hydride functionality and the other will feature the polymer with vinyl functionality). The two parts, A and B, are mixed in 3:1 by weight ratio, respectively.

50% v/v microspheres dispersion (posterior) was prepared as follows. In a 200 cc glass beaker the following chemicals were added:

63.66 gr of MED3-6300 Part A.
21.22 gr of MED3-6300 Part B.

All of the components were mixed by magnetic stirring thoroughly until a homogenous solution was obtained. The obtained solution was sonicated for 4-8 min in a bath sonicator in order to increase mixing efficiency, avoid agglomeration and degas the solution. During sonication, the solution was mixed. The obtained solution was degassed using a desiccator vessel with vacuum less than 0.01 bar.

14 gr of microspheres were dried in an oven at 150° C. for 20-30 min. During the drying operation, the microspheres were agitated periodically.

The dried microspheres were added to the Silicone solution immediately after drying. Drying the microspheres immediately before use is helpful to reduce any moisture on the surface of the microspheres and to allow the microsphere/gel interface to have as complete contact as possible along the surface of the microspheres. All components were mixed by magnetic stirring thoroughly until a homogenous solution was obtained.

The resultant solution was sonicated in order to increase mixing efficiency, avoid agglomeration and degas the solution. During sonication, the solution was mixed.

The resultant solution was degassed under vacuum of less than 0.01 bar.

30% v/v microspheres dispersion (anterior) was prepared similarly, except that a different Silicone composition was used as follows, to adjust for lower percentage of microspheres:

78.21 gr of MED3-6300 Part A.
26.07 gr of MED3-6300 Part B.

Also only 10.32 gr of microspheres were used, to obtain the lower percentage of microspheres in the final composite material.

Each of the above composite materials was then immediately filled into their respective shells (lumens). The posterior lumen was prepared with a 175 cc sealed shell (shell and patching parts) and was filled with the above described 50% v/v microspheres dispersion using a syringe. Excess air in the shell was then removed with a syringe. Sonication and degassing of the solution in the filled shell was performed to enable more air to be removed.

The filled lumen was then placed in an oven and rotated along an axis for about ~2 rpm during curing at 150° C. for 5 hours. For this Example, a skewer was used to enable rotation of the lumen attached at the surface. Delay between filling and curing was avoided to prevent phase separation.

The anterior lumen was prepared similarly except that a 390 cc open shell (shell without a complete external patch, with access to the interior) was used. The gel cured posterior lumen was attached to the anterior lumen at the center of radial axes of the anterior lumen in such a way that both lumens were concentric. The anterior lumen was filled with the 30% v/v microspheres dispersion using a syringe and the process was performed as described for the posterior lumen, including curing.

Figure 6:
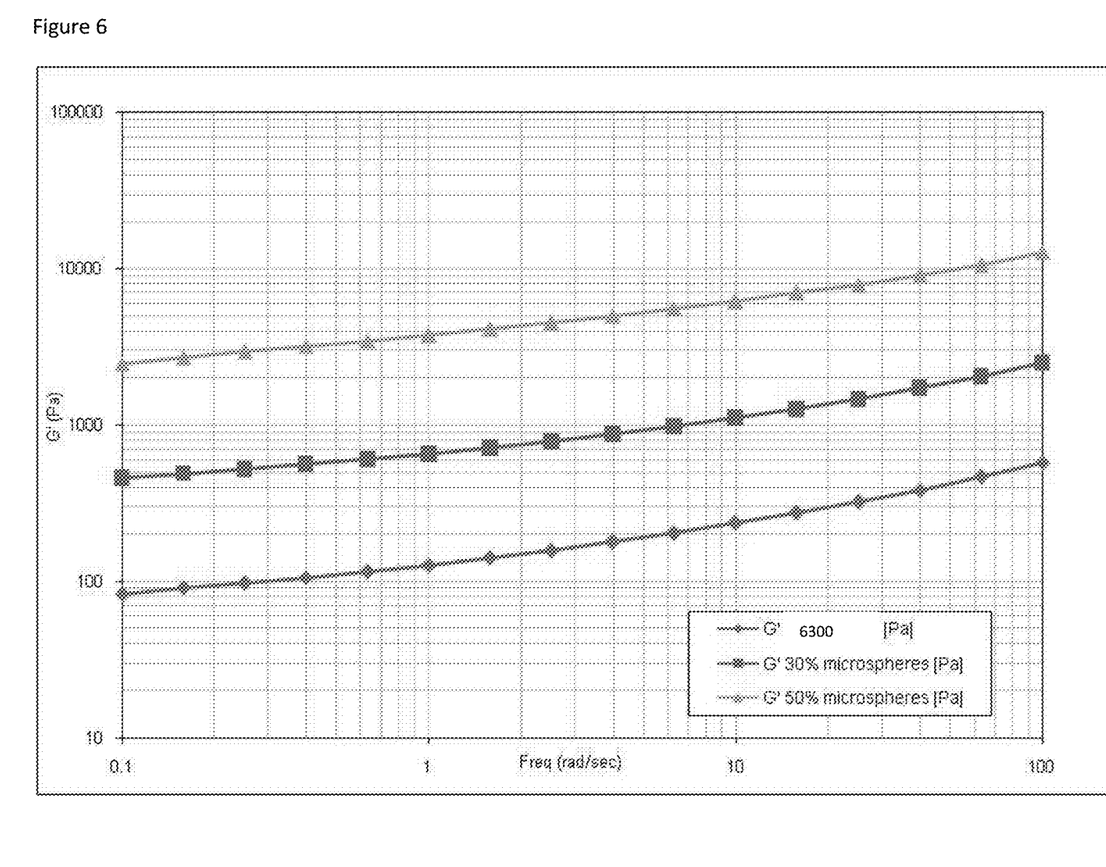
FIG. 6 shows the results of a dynamic (sinusoidal) simple shear flow experiment where a small cyclic deformation is imposed upon the sample and the stress response is measured.

Test amounts of the gel containing 30% and 50% microspheres were cured (outside of the shell) and were tested for storage modulus (G') as indication of cohesiveness and elastic modulus, through performance of a dynamic (sinusoidal) simple shear flow experiment where a small cyclic deformation is imposed upon the sample and the stress response is measured. Viscoelastic properties (i.e. storage modulus (G') and loss modulus (G")) are determined via this type of dynamic test. The storage modulus (G') is indicative of the strength of the elastic modulus and thus gel cohesiveness. FIG. 6 shows the results of such testing, in which the lowest line (diamonds) relates to the gel alone, without microspheres; the middle line (squares) shows gel with 30% microspheres; and the top line (triangles) shows gel with 50% microspheres. As shown, as the percentage of microspheres increases, the gel/microsphere composite material shows increasing storage modulus. Such increased strength both increases the likelihood of the composite material maintaining its coherency if trauma occurs (such as a physical blow to the material, or to tissue containing the material) and also means that the gel/microsphere bond is stronger than the gel/gel bond, such that even if the composite material is cleaved, the surrounding tissue will be shielded from exposure to the microspheres themselves.

While the invention has been described with respect to a limited number of embodiments, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A composite material comprising a polymeric gel and a plurality of additives, wherein said additives have been surface treated prior to incorporation with said polymeric gel with a surface treatment comprising at least one of organofunctional silanes, organofunctional titanates, organofunctional zirconates or long chain fatty acids;
   wherein said additives comprise a plurality of micro-lumens, and wherein said micro-lumens are rigid and comprise ceramic or glass;
   wherein said additives that have been surface treated prior to incorporation with said polymeric gel and said gel undergo a curing reaction to cross-link said surface treated additives to said gel; and wherein the composite material is suitable for implantation to the human body.

2. The composite material of claim 1, wherein said polymeric gel comprises a silicone gel.

3. The material of claim 1, wherein said micro-lumens comprise up to 60% of the composite material.

4. The material of claim 1, wherein the composite material has a modulus of up to about 100 times that of the cured polymeric gel without the additives.

5. The composite material of claim 4, wherein said organofunctional silanes include a propyl functional group.

6. The composite material of claim 5, wherein said organofunctional silanes include n-propyltrimethoxysilane.

7. The material of claim 1, wherein a strength of adhesion between gel and additives is stronger than said strength of adhesion within said gel.

8. The material of claim 1, wherein said gel comprises a gel network and wherein said additives are integrated into said gel network.

9. The material of claim 1, wherein said surface treatment undergoes addition reaction with said gel during a curing reaction.

10. The material of claim 1, wherein said surface treatment undergoes addition reaction or addition polymerization with said gel during a curing reaction.

* * * * *